United States Patent
Dawson

(10) Patent No.: US 6,173,713 B1
(45) Date of Patent: Jan. 16, 2001

(54) EYE PATCH CONSTRUCTION METHOD

(76) Inventor: Charles R. Dawson, 4625 Anson St., New Orleans, LA (US) 70131

( * ) Notice: Under 35 U.S.C. 154(b), the term of this patent shall be extended for 0 days.

(21) Appl. No.: 09/533,134

(22) Filed: Mar. 23, 2000

(51) Int. Cl.[7] .................................................. A61F 9/00
(52) U.S. Cl. .................................................. 128/858; 2/15
(58) Field of Search .................................. 128/846, 857, 128/858; 2/12, 15

(56) References Cited

U.S. PATENT DOCUMENTS

| | | | |
|---|---|---|---|
| 3,619,815 | * 11/1971 | Towner | 128/858 |
| 4,944,040 | * 7/1990 | Riedel | 128/858 |
| 4,995,114 | * 2/1991 | Price | 128/858 |
| 5,191,897 | * 3/1993 | Meshel | 128/858 |
| 5,487,394 | * 1/1996 | Shiu | 128/858 |

* cited by examiner

Primary Examiner—Michael A. Brown
(74) Attorney, Agent, or Firm—Joseph N. Breaux

(57) ABSTRACT

An eye patch construction method for constructing an eye patch that adheres to the skin surface surrounding the eye to be covered but which leaves no residue on the skin surface to be cleaned.

1 Claim, 1 Drawing Sheet

ABSTRACT AND BODY TEXT:

EYE PATCH CONSTRUCTION METHOD

TECHNICAL FIELD

The present invention relates to eye care products and more particularly to an eye patch construction method that includes the steps of: a) providing a quantity of a non-residue leaving, adhering, silicon polymer putty; b) providing an eyeglass assembly including two eye glass lenses held in an eye glass frame, each eye glass lens having an eye facing surface and an object facing surface; c) molding the quantity of non-residue leaving, adhering, silicon polymer putty over the eye to be covered such that light is prevented from entering the eye; and d) positioning the eyeglass assembly onto the face such that the non-residue leaving, adhering, silicon putty is adhered to the eye facing surface of one of the eye glass lens and to skin surrounding the eye to be covered such that light is prevented from entering the eye.

BACKGROUND ART

It is often necessary for individuals suffering from lazy eye and other ocular problems to wear an eye patch for an extended period of time. These eye patches are often adhesively held in place and leave a residue on the skin surface which is difficult to remove. It would be a benefit, therefore, to have an eye patch that would adhere to the skin surface but which would leave no residue on the skin surface to be cleaned.

GENERAL SUMMARY DISCUSSION OF INVENTION

It is thus an object of the invention to provide an eye patch construction method that includes the steps of: a) providing a quantity of a non-residue leaving, adhering, silicon polymer putty; b) providing an eyeglass assembly including two eye glass lenses held in an eye glass frame, each eye glass lens having an eye facing surface and an object facing surface; c) molding the quantity of non-residue leaving, adhering, silicon polymer putty over the eye to be covered such that light is prevented from entering the eye; and d) positioning the eyeglass assembly onto the face such that the non-residue leaving, adhering, silicon putty is adhered to the eye facing surface of one of the eye glass lens and to skin surrounding the eye to be covered such that light is prevented from entering the eye.

Accordingly, an eye patch construction method is provided. The eye patch construction method includes eye patch construction method that includes the steps of: a) providing a quantity of a non-residue leaving, adhering, silicon polymer putty; b) providing an eyeglass assembly including two eye glass lenses held in an eye glass frame, each eye glass lens having an eye facing surface and an object facing surface; c) molding the quantity of non-residue leaving, adhering, silicon polymer putty over the eye to be covered such that light is prevented from entering the eye; and d) positioning the eyeglass assembly onto the face such that the non-residue leaving, adhering, silicon putty is adhered to the eye facing surface of one of the eye glass lens and to skin surrounding the eye to be covered such that light is prevented from entering the eye.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 2:
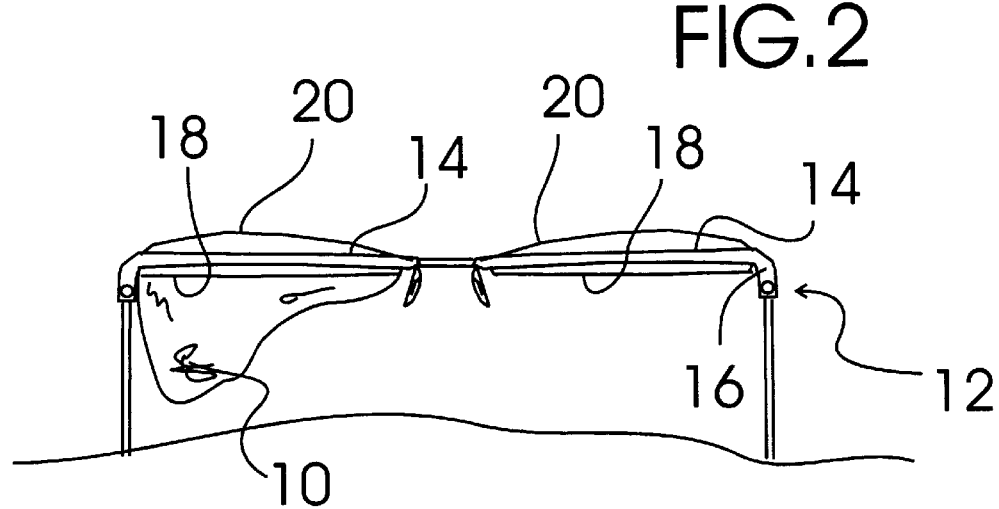
FIG. 2 is a top plan view showing a quantity of the non-residue leaving, adhering, silicon polymer putty attached to the eye facing surface of an eye glass lens and shaped to form an eye area conforming eye patch.
Figure 3:
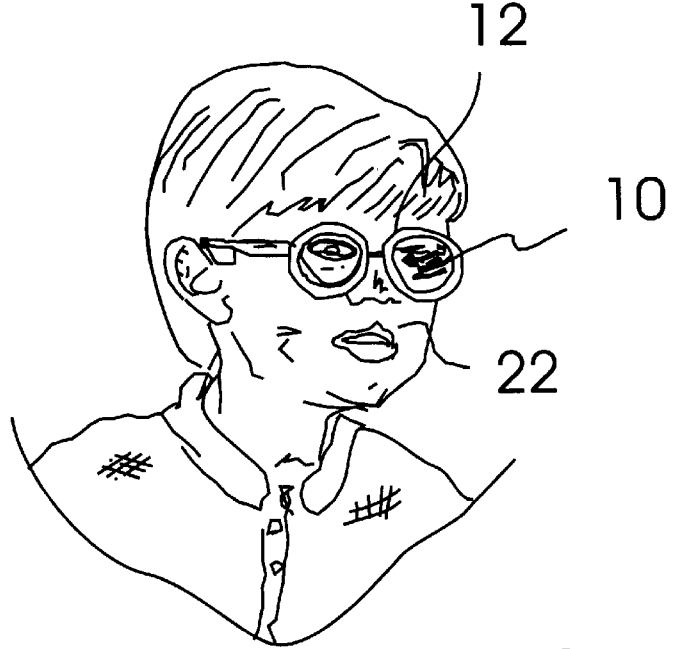
FIG. 3 is a perspective view showing a representative child wearing an eye patch constructed according to the method of the present invention.
Figure 1:
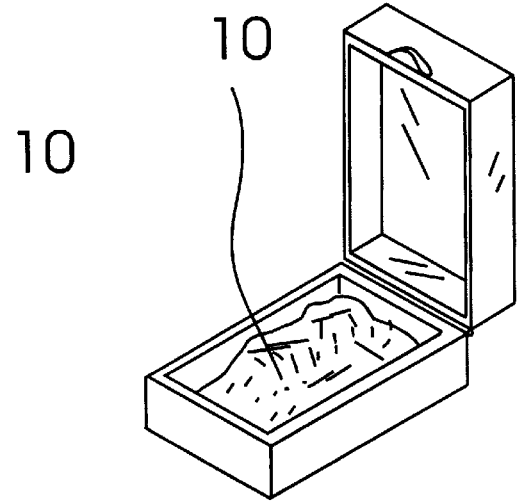
FIG. 1 is a perspective view of a quantity of the non-residue leaving, adhering, silicon polymer putty provided in the eye patch construction method of the present invention stored within a storage box.

FIGS. 1–3 show various aspects of an exemplary embodiment of the eye patch construction method of the present invention. The exemplary eye patch construction method includes the steps of: a) providing a quantity of a non-residue leaving, adhering, silicon polymer putty, generally designated 10; b) providing an eyeglass assembly, generally designated 12, including two eye glass lenses 14 held in an eye glass frame 16, each eye glass lens 14 having an eye facing surface 18 and an object facing surface 20; c) molding the quantity of non-residue leaving, adhering, silicon polymer putty 10 over the eye to be covered such that light is prevented from entering the eye; and d) positioning the eyeglass assembly 12 onto the face 22 such that the non-residue leaving, adhering, silicon putty 10 is adhered to the eye facing surface 18 of one of the eye glass lens 14 and to skin surrounding the eye to be covered such that light is prevented from entering the eye. In this embodiment the non-residue leaving, adhering, silicon polymer putty 10 provided is Dow Corning 3179 Dilatant Compound which is coral colored and commercially available in 50 pound cartons. Another similar material is marketed as Silly Putty® by Binney & Smith Inc., Easton Pa.

It can be seen from the preceding description that an eye patch construction method has been provided.

It is noted that the embodiment of the eye patch construction method described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An eye patch construction method comprising the steps of:
   a) providing a quantity of a non-residue leaving, adhering, silicon polymer putty;
   b) providing an eyeglass assembly including two eye glass lenses held in an eye glass frame, each eye glass lens having an eye facing surface and an object facing surface;
   c) molding the quantity of non-residue leaving, adhering, silicon polymer putty over the eye to be covered such that light is prevented from entering the eye; and
   d) positioning the eyeglass assembly onto the face such that the non-residue leaving, adhering, silicon putty is adhered to the eye facing surface of one of the eye glass lens and to skin surrounding the eye to be covered such that light is prevented from entering the eye.

* * * * *